United States Patent [19]

Ghebre-Sellassie et al.

[11] Patent Number: 5,281,421
[45] Date of Patent: Jan. 25, 1994

[54] GEMFIBROZIL FORMULATIONS

[75] Inventors: Isaac Ghebre-Sellassie, Stanhope; Mahdi B. Fawzi, Flanders, both of N.J.

[73] Assignee: Warner-Lambert Company, Morris Plains, N.J.

[21] Appl. No.: 873,511

[22] Filed: Apr. 16, 1992

Related U.S. Application Data

[63] Continuation of Ser. No. 539,158, Jun. 15, 1990, abandoned.

[51] Int. Cl.$^5$ ................................................ A61K 9/20
[52] U.S. Cl. ............................ 424/465; 424/440; 424/452; 514/824; 514/929; 514/960; 514/975
[58] Field of Search .............. 424/452, 465, 440; 514/824, 929, 960, 975

[56] References Cited

U.S. PATENT DOCUMENTS

| | | | |
|---|---|---|---|
| 4,344,934 | 8/1982 | Martin et al. | 424/80 |
| 4,620,974 | 11/1986 | Hersh et al. | 424/453 |
| 4,716,033 | 12/1987 | Denick, Jr. | 424/440 X |
| 4,753,800 | 6/1988 | Mozda | 424/440 |
| 4,778,676 | 10/1988 | Yang et al. | 424/79 |
| 4,814,354 | 3/1989 | Ghebre-Sellassie et al. | 424/440 |
| 4,816,264 | 3/1989 | Phillips et al. | 424/468 |
| 4,865,850 | 9/1989 | Shell et al. | 424/491 |
| 4,891,220 | 1/1990 | Donzis | 424/88 |
| 4,895,726 | 1/1990 | Curtet et al. | 424/456 |
| 4,929,605 | 5/1990 | Domet et al. | 424/465 |
| 4,971,804 | 11/1990 | Ghebre-Sellasie et al. | 424/490 |
| 5,023,088 | 6/1991 | Wong et al. | 424/473 |
| 5,126,348 | 6/1992 | McMurray | 514/264 |

FOREIGN PATENT DOCUMENTS

261693A1 3/1988 European Pat. Off. .
295637A2 12/1988 European Pat. Off. .
WO8805296 7/1988 PCT Int'l Appl. .

*Primary Examiner*—Paul R. Michl
*Assistant Examiner*—Robert H. Harrison
*Attorney, Agent, or Firm*—Michael J. Atkins

[57] ABSTRACT

Improved oral formulations are prepared by admixing gemfibrozil with from 1 to 4%, by weight, of a pharmaceutically acceptable surfactant having an HLB value of from about 10 to about 50.

12 Claims, No Drawings

GEMFIBROZIL FORMULATIONS

CROSS-REFERENCE TO RELATED APPLICATIONS

This application is a continuation of U.S. Ser. No. 07/539,158 filed Jun. 15, 1990, now abandoned.

The present invention relates to improved formulation of gemfibrozil.

BACKGROUND

Gemfibrozil, or 5-(2,5-dimethylphenoxy)-2,2-dimethylpentanoic acid, is a widely used antihyperlipoproteinemic agent. Physically the chemical is a crystalline material which melts in the range of 61° to 63° C. (hexane) and exhibits a boiling point of $158°-159°_{0.02}C$. The substance is nonhygroscopic and generally compatible with common pharmaceutical excipients but has very poor solubility in water. This is particularly true in a highly acidic medium (such as is encountered in the stomach) since its apparent pKa is 4.7.

The typical daily dose is high, generally about 1200 mg, probably because of the poor water solubility. This dosage generally is administered using for example two capsules of 300 mg or a single compressed tablet of 600 mg, administration in each case being b.i.d.

The present invention pertains to improvements in gemfibrozil formulations which improve the compound's dissolution profile and thus increase the drug's blood levels upon oral administration.

U.S. Pat. No. 4,716,033 discloses a medicament adsorbate such as magnesium aluminum silicate having a medicament, including inter alia gemfibrozil, and surfactant adsorbed thereon.

U.S. Pat. No. 4,753,800 discloses a medicament adsorbate having a medicament, including inter alia gemfibrozil, dispersed in an edible wax adsorbed thereon.

U.S. Pat. No. 4,814,354 discloses pharmaceutical compositions of an anion exchange resin lipid regulator, such as cholestyramine or cholestipol, and gemfibrozil.

U.S. Pat. No. 4,778,676 discloses a chewable confection delivery system of coated cholestyramine and a confectionery matrix..

U.S. Pat. No. 4,816,264 discloses an oral delivery system having a core portion of drug and a cellulosic gelling polymer and a semipermeable membrane around the core.

U.S. Pat. No. 4,865,850 discloses a method of expelling fat from the gastrointestinal tract by administering non-biodegradable collagen particles having fat receptors, including inter alia gemfibrozil, on their surface.

EP-A 295,637 A2 discloses pharmaceutical compositions in which a lipid regulating component, including inter alia gemfibrozil, is combined with inhibitor of acylCoA:cholesterol acyltransferase. EP-A 261,693 A1 discloses a lipid regulating component, including inter alia gemfibrozil, which has been pretreated to render it stale until such time as it reaches the proximal section of the intestines.

PCT WO 88/05296 discloses pharmaceutical compositions in which a lipid regulating component, including inter alia gemfibrozil, is combined with inhibitor of 3-hydroxy-3-methylglutaryl coenzyme A reductase.

Commercially available gemfibrozil capsules contain a small amount of sodium lauryl sulfate, typically less than 0.2%. Compressed tablets of gemfibrozil which are commercially available contain somewhat more but again less than 1%; e.g., 0.7%.

DETAILED DESCRIPTION

The present invention is based on the discovery when gemfibrozil is admixed with from 1 to 4%, by weight of gemfibrozil, of a pharmaceutically acceptable surfactant having a hydrophilic-lipophilic balance value ("HLB") of from about 10 to about 50, significant improvements in the rate of dissolution in both acid and alkaline media are observed.

Suitable pharmaceutically acceptable surfactants having an HLB value of from about 10 to about 50 include polysorbates, pluronics, alkali metal salts of fatty alcohol sulfates, such as sodium lauryl sulfate, salts of fatty acids such as sodium oleate and triethanolamine oleate, and the like. The following list exemplifies typical surfactants and their HLB values:

| Surfactant | HLB |
| --- | --- |
| Pluronic F68 | 29.0 |
| Sodium oleate | 18.0 |
| Tween 20 | 16.7 |
| Tween 40 | 15.6 |
| Tween 80 | 15.0 |
| Tween 60 | 14.8 |
| Tween 21 | 13.3 |
| Triethanolamine oleate | 12.0 |
| Tween 85 | 11.0 |
| Tween 65 | 10.5 |
| Tween 81 | 10.0 |

A preferred ratio utilizes from 1% to about 2% of the surfactant. In addition, the pharmaceutically acceptable surfactant preferably has an HLB value of from about 15 to about 40.

Generally the indicated amount of surfactant is dissolved with the amount of water ultimately required for granulation of the gemfibrozil. The gemfibrozil, together with any other excipients to be granulated such as silicon dioxide, hydroxypropyl cellulose starch, and the like is then granulated in this aqueous solution. After granulation and drying, any other dry ingredients, as for example microcrystalline starch, lubricants such as calcium stearate, additional silicon dioxide, and the like, are added and blended and the mixture then compressed into tablets.

The following is a typical formulation:

| | |
| --- | --- |
| Gemfibrozil | 600.00 g |
| Silicon Dioxide | 12.00 g |
| Hydroxypropyl cellulose | 16.00 g |
| Pregelatinized starch 1551 | 141.00 g |

The foregoing components, including the active ingredient and the granulation additives, are milled through a #0 screen and blended with 141.00 g of pregelatinized starch 1551. This mixture then is granulated with a solution of the selected surfactant (indicated below) in 100 mL of purified water USP. The granulation is dried, combined with an additional 10.00 g of silicon dioxide, remilled through a Fitzmill No. 2A RH screen and then blended with 64.80 g of granular microcrystalline cellulose and 10.00 g of calcium stearate.

Aliquots of 860 mg are punched on 0.745"×0.360" elliptical punches at a hardness of 12 to 16 kp and about 0.300" gauge.

Tablets prepared in the foregoing manner were tested to evaluate their rate of dissolution in various media: 0.1N hydrochloric acid, 0.05M phosphate buffer at two pH values (5.5 and 7.4), and 0.2 phosphate buffer at pH 7.4. the results are as follows:

| Time (minutes) | Amount of Surfactant | | | |
|---|---|---|---|---|
| | 0.0% | 0.5% | 1.0% | 2.0% |
| | % Dissolved | | | |
| (1) 0.1N Hydrochloric Acid | | | | |
| Polysorbate 80 | | | | |
| 5 | 0.3 | 0.9 | 1.4 | 1.7 |
| 10 | 0.5 | 1.0 | 1.8 | 2.2 |
| 20 | 0.8 | 1.3 | 2.2 | 2.5 |
| 30 | 1.2 | 1.5 | 2.3 | 2.6 |
| 40 | 1.5 | 1.7 | 2.4 | 2.7 |
| 50 | 1.7 | 1.9 | 2.5 | 2.7 |
| 60 | 1.9 | 2.0 | 2.5 | 2.7 |
| Sodium Lauryl Sulfate | | | | |
| 5 | 0.3 | 1.0 | 0.8 | 1.5 |
| 10 | 0.5 | 1.1 | 1.1 | 1.9 |
| 20 | 0.8 | 1.6 | 1.7 | 2.2 |
| 30 | 1.2 | 2.0 | 2.0 | 2.2 |
| 40 | 1.5 | 2.1 | 2.2 | 2.3 |
| 50 | 1.7 | 2.2 | 2.3 | 2.3 |
| 60 | 1.9 | 2.4 | 2.3 | 2.3 |
| (2) 0.05M Phosphate Buffer (pH 5.5) | | | | |
| Polysorbate 80 | | | | |
| 5 | 0.13 | 0.6 | 3.9 | 8.0 |
| 10 | 0.7 | 0.7 | 6.5 | 10.5 |
| 20 | 1.9 | 3.6 | 9.4 | 11.7 |
| 30 | 3.2 | 5.3 | 10.6 | 11.9 |
| 40 | 4.4 | 6.8 | 11.2 | 12.1 |
| 50 | 5.5 | 8.0 | 11.3 | 12.1 |
| 60 | 6.4 | 8.9 | 11.5 | 12.1 |
| Sodium Lauryl Sulfate | | | | |
| 5 | 0.1 | 1.8 | 1.4 | 5.4 |
| 10 | 0.7 | 2.1 | 2.8 | 7.6 |
| 20 | 1.9 | 3.4 | 5.1 | 9.7 |
| 30 | 3.2 | 4.6 | 7.0 | 10.6 |
| 40 | 4.4 | 5.8 | 8.3 | 11.0 |
| 50 | 5.5 | 6.8 | 9.3 | 11.2 |
| 60 | 6.4 | 7.7 | 9.9 | 11.3 |
| (3) 0.05M Phosphate Buffer (pH 7.4) | | | | |
| Polysorbate 80 | | | | |
| 5 | 12.2 | 23.9 | 57.5 | 82.3 |
| 10 | 23.8 | 44.0 | 78.9 | 95.0 |
| 20 | 43.3 | 69.0 | 94.6 | 99.5 |
| 30 | 58.5 | 83.7 | 98.4 | 100.0 |
| 40 | 69.1 | 92.5 | 99.4 | 100.0 |
| 50 | 77.0 | 97.7 | 100.0 | 100.0 |
| 60 | 82.9 | 100.6 | 100.0 | 100.0 |
| Sodium Lauryl Sulfate | | | | |
| 5 | 12.2 | 22.1 | 27.8 | 68.2 |
| 10 | 23.8 | 42.4 | 51.9 | 86.5 |
| 20 | 43.3 | 69.0 | 80.1 | 100.0 |
| 30 | 58.5 | 83.5 | 92.6 | 100.0 |
| 40 | 69.1 | 91.1 | 97.4 | 100.0 |
| 50 | 77.0 | 95.1 | 100.0 | 100.0 |
| 60 | 82.9 | 97.2 | 100.0 | 100.0 |
| (4) 0.2M Phosphate Buffer (pH 7.4) | | | | |
| Polysorbate 80 | | | | |
| 5 | 17.9 | 21.6 | 62.1 | 87.7 |
| 10 | 33.0 | 42.0 | 84.8 | 96.2 |
| 20 | 56.8 | 68.7 | 97.3 | 100.0 |
| 30 | 73.1 | 84.4 | 99.6 | 100.0 |
| 40 | 83.7 | 92.9 | 100.0 | 100.0 |
| 50 | 90.8 | 97.6 | 100.0 | 100.0 |
| 60 | 95.4 | 100.0 | 100.0 | 100.0 |
| Sodium Lauryl Sulfate | | | | |
| 5 | 17.9 | 30.5 | 46.3 | 82.0 |
| 10 | 33.0 | 56.4 | 74.4 | 91.5 |
| 20 | 56.8 | 85.0 | 94.5 | 100.0 |
| 30 | 73.1 | 95.0 | 98.7 | 100.0 |
| 40 | 83.7 | 98.4 | 99.7 | 100.0 |
| 50 | 90.8 | 99.7 | 100.0 | 100.0 |
| 60 | 95.4 | 100.0 | 100.0 | 100.0 |

As can be seen from the above, the incorporation of the surfactant significantly increases the rate of dissolution in otherwise identical formulations over a wide range of pH values.

What is claimed is:

1. A gemfibrozil tablet consisting of gemfibrozil as the pharmaceutically active ingredient wherein the gemfibrozil is admixed with from 1 to 4%, by weight of the gemfibrozil, of a pharmaceutically acceptable surfactant having an HLB value of from about 10 to about 50.

2. A gemfibrozil tablet according to claim 1 wherein the amount of surfactant is from 1% to about 2%.

3. A gemfibrozil tablet according to claim 1 wherein the pharmaceutically acceptable surfactant has an HLB value of from about 15 to about 4.

4. A gemfibrozil tablet according to claim 1 wherein the pharmaceutically acceptable surfactant is a polysorbate.

5. A gemfibrozil tablet according to claim 1 wherein the pharmaceutically acceptable surfactant is an alkali metal salt of a fatty alcohol sulfate.

6. A gemfibrozil tablet according to claim 5 wherein the pharmaceutically acceptable surfactant is sodium lauryl sulfate.

7. A gemfibrozil tablet consisting of gemfibrozil as the pharmaceutically active ingredient wherein the gemfibrozil is admixed with from 1 to 4%, by weight of gemfibrozil, of a pharmaceutically acceptable surfactant having an HLB value of from about 10 to about 50, the incorporation of a surfactant increasing the rate of dissolution of the gemfibrozil in acid or alkaline media.

8. A gemfibrozil tablet according to claim 7 wherein the amount of surfactant is from 1% to about 2%.

9. A gemfibrozil tablet according to claim 7 wherein the pharmaceutically acceptable surfactant has an HLB value of from about 15 to about 40.

10. A gemfibrozil tablet according to claim 7 wherein the pharmaceutically acceptable surfactant is a polysorbate.

11. A gemfibrozil tablet according to claim 7 wherein the pharmaceutically acceptable surfactant is an alkali metal salt of a fatty alcohol sulfate.

12. A gemfibrozil tablet according to claim 11 wherein the pharmaceutically acceptable surfactant is sodium lauryl sulfate.

* * * * *